United States Patent [19]

Baker et al.

[11] Patent Number: 4,767,792

[45] Date of Patent: Aug. 30, 1988

[54] PROCESS FOR CATALYTICALLY CONVERTING A CARBON MONOXIDE-AND HYDROGEN-CONTAINING FEED STREAM INTO HYDROCARBONS

[75] Inventors: Bruce G. Baker, Torrens Park; Neville J. Clark; Hamish McArthur, both of Bellevue Heights; Edward Summerville, Everard Park, all of Australia

[73] Assignee: The Flinders University of South Australia, Bedford Park, Australia

[21] Appl. No.: 16,353

[22] Filed: Feb. 19, 1987

Related U.S. Application Data

[60] Division of Ser. No. 831,553, Feb. 20, 1986, Pat. No. 4,666,880, which is a continuation of Ser. No. 604,655, filed as PCT AU83/00110 on Aug. 19, 1983, published as WO84/00702 on Mar. 1, 1984, Pat. No. 4,610,975.

[30] Foreign Application Priority Data

Aug. 19, 1982 [AU] Australia .............................. PF5478

[51] Int. Cl.$^4$ .............................................. C07L 1/04
[52] U.S. Cl. ................................................... 518/721
[58] Field of Search ......................................... 518/721

[56] References Cited

U.S. PATENT DOCUMENTS 2,211,022 8/1940 Michael .............................. 518/721

FOREIGN PATENT DOCUMENTS 105848 12/1938 Australia .

Primary Examiner—Howard T. Mars
Attorney, Agent, or Firm—Cushman, Darby & Cushman

[57] ABSTRACT

A method of forming a support for use with a primary catalyst for conversion of a feed stream comprising carbon monoxide and hydrogen into hydrocarbons is disclosed.

A primary catalyst and a method of manufacturing the catalyst is also disclosed.

Furthermore, a secondary catalyst for the production of branched chain alkenes from straight chain alkenes is also disclosed, together with methods of manufacturing the secondary catalyst.

3 Claims, 2 Drawing Sheets

PROCESS FOR CATALYTICALLY CONVERTING A CARBON MONOXIDE-AND HYDROGEN-CONTAINING FEED STREAM INTO HYDROCARBONS

This is a division of application Ser. No. 831,553 filed Feb. 20, 1986, now U.S. Pat. No. 4,666,880 which is a continuation of Ser. No. 604,655, filed as PCT AU83/00110 on Aug. 19, 1983, published as WO84/00702 on Mar. 1, 1984, now U.S. Pat. No. 4,610,975.

The present invention relates to the production of hydrocarbons. In particular, the present invention relates to primary and secondary catalysts for use in the Fischer-Tropsch process for synthesising hydrocarbons adapted for gasoline production and to supports for such primary catalysts.

DESCRIPTION OF THE INVENTION

Figure 1:
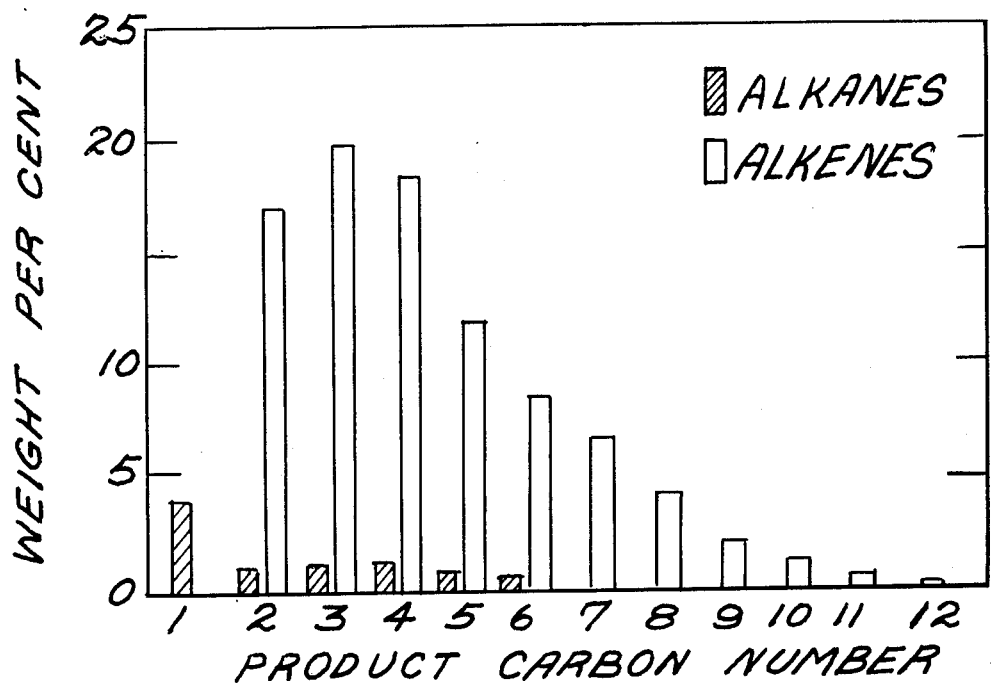
FIG. 1 is a plot of the weight percent of products versus product carbon number.

The Fischer-Tropsch process is one of the major processes for producing synthetic hydrocarbons. The process is biased on the use of carbon monoxide and hydrogen which can both be readily derived from gasification of coal or char or by steam reforming of natural gas. The process relies on catalytic synthesis and basically comprises passing a gaseous feed stream of carbon monoxide and hydrogen over a catalyst bed. The catalyst and process operating conditions are selected so that one or other of the following reactions predominates:

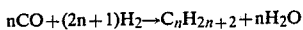

$nCO + (2n+1)H_2 \rightarrow C_nH_{2n+2} + nH_2O$

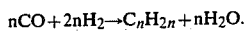

$nCO + 2nH_2 \rightarrow C_nH_{2n} + nH_2O$.

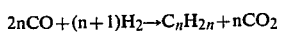

$2nCO + (n+1)H_2 \rightarrow C_nH_{2n} + nCO_2$

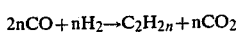

$2nCO + nH_2 \rightarrow C_2H_{2n} + nCO_2$

The Fischer-Tropsch process is subject to a number of limitations. One limitation is that the hydrocarbons produced by the process include a significant proportion of straight chain hydrocarbons of low octane number. Various processes have been proposed to improve the octane number of the hydrocarbons, and thus the suitability for use in gasoline production, by converting the straight chain hydrocarbons into branched hydrocarbons. However, the known processes tend to be expensive and are not adapted to form part of a continuous process with the Fischer-Tropsch process.

Another limitation is that it is difficult to control the process reaction to selectively form hydrocarbons having carbon numbers suitable for use in gasoline production. One reason for this particular limitation of the Fischer-Tropsch process is the selection of catalysts for use in the process. Iron is a major component of most exiting commercial catalysts, and although it is active as a catalyst, the hydrocarbons produced cover a wide distribution of carbon numbers, many of which are not suitable for gasoline production. For example, depending on the process conditions, the hydrocarbons produced include significant proportions of either low carbon number gaseous products or high carbon number straight chain products which form as waxes. Both products are generally not suitable for use in gasoline production.

One object of the present invention is to provide an improved primary and an improved secondary catalyst, improved methods for the manufacture of the catalysts, improved supports for the primary catalyst and improved processes for using the catalysts which alleviate the disadvantages described in the preceding paragraphs.

According to the present invention there is provided a method of forming a support for use with a primary catalyst for conversion of a feed stream comprising carbon monoxide and hydrogen into hydrocarbons, said method comprising heat treating γ-alumina at a predetermined temperature for a predetermined time to form a material having a crystallographic structure predominantly indicative of α-alumina, a surface area intermediate between γ-alumina and α-alumina, said material exhibiting basic properties at the surface thereof.

Preferably, the temperature is greater than 1100° C. and the time is less than 2 hour. It is particularly preferred that the temperature is 1250° C. and the time is 10 minutes.

According to the present invention there is also provided a support for use with a primary catalyst for conversion of a feed stream comprising carbon monoxide and hydrogen into hydrocarbons formed by the method described above.

According to the present invention there is provided a primary catalyst for conversion of a feed stream comprising carbon monoxide and hydrogen into hydrocarbons, said catalyst comprising a support, an active component impregnated on the support for catalysing a reaction in the feed stream to produce hydrocarbons, and a modifier component impregnated on the support to modify the catalytic behaviour of the active component to control the length of hydrocarbon chains formed by the said reaction.

Preferably, the modifier component causes the active component to catalyse the reaction in the feed stream so that a significant proportion of the hydrocarbons formed have carbon numbers between 3 and 8. Preferably, the reaction is modified so that greater than 90% of the hydrocarbons have carbon numbers between 2 and 8 and less than 6% of the hydrocarbons comprise methane. It is also preferred that the reaction is modified so that a significant proportion of the hydrocarbons comprise 1-alkenes.

The active component is preferably iron.

The modifier component may comprise a rare earth metal. In a particularly preferred form the rare earth metal is praseodymium present alone, or present with other rare earth metals in mixed rare earth oxides such as naturally occurring rare earth oxides. It is preferred that the weight-percent of rare earths be in excess of the weight-percent of the iron. We use the expression "rare earth metals" in this specification and in the appended claims to include lanthanum.

It is preferred that the catalyst be supported. The support for the catalyst is preferably in granular form, to suit the particular process conditions. The support may comprise:

(i) a high area acidic support which tends to limit chain growth, for example gamma-alumina, or (ii) a relatively low area but substantially inert support, for example alpha-alumina.

(iii) in the preferred form the support is prepared by heating a γ-alumina rapidly to a high temperature, preferably above 1200° C., maintaining it at high temperature for a limited time.

In this connection, the present invention also provides a method of manufacturing the primary catalyst described above on a support, the method comprising forming a coating of the modifier component on the support and simultaneously with or subsequently forming a coating of the active component on the support, there being at least some contact between the coating of the modifier component and the coating of the active component.

In one preferred embodiment, in which the active component comprises iron and the modifier component comprises praseodymium, the respective coatings are formed on the support by absorption from separate or mixed solutions of salts of praseodymium and iron, and the salts are separately decomposed by heating to form praseodymium oxide and iron oxides and reduced and pretreated in a stream of hydrogen below 400° C.

The present invention also provides a process for converting a feed stream comprising carbon monoxide and hydrogen into hydrocarbons, the process comprising passing the feed stream over the primary catalyst described above. It has been found that when using the primary catalyst described above a significant proportion of the hydrocarbons formed by the process comprise carbon numbers between 3 and 8. In particular, it has been found that greater than 90% of the hydrocarbons formed by the process have carbon numbers between 2 and 8 and that less than 6% of the hydrocarbons formed comprise methane. It has also been found that a significant proportion of the hydrocarbons formed comprise 1-alkenes.

According to the present invention there is also provided a secondary catalyst for the production of branched chain alkenes from straight chain alkenes, the catalyst comprising an intermediate oxide of tungsten in which the average valence state of the tungsten radical is greater than 4 and less than 6, the surface having been activated at a predetermined oxygen partial pressure to cause skeletal isomerisation of straight chain alkenes to form branched chain alkenes at that predetermined oxygen partial pressure.

In a particularly preferred form the average valence state of the tungsten radical is $5.6 \pm 0.2$.

It has been found that the secondary catalyst catalyses the following reactions to form branched chain alkenes:

(a) 1-alkenes having carbon numbers up to 8 double bond shift to form 2-alkenes and then form branched chain alkenes, each with at least one methyl group adjacent the double bond.

(b) 2-alkenes form branched chain alkenes, each with at lest one methyl group adjacent the double bond.

(c) 1-alkenes having carbon numbers greater than 8 are cracked to form alkenes having carbon numbers between 4 and 8, the alkenes double bond shift and then carbon bond skeletal isomerise to form branched chain alkenes.

The invention also provides a method for the manufacture of the secondary catalyst, the method comprising oxidising tungsten metal with a gas atmosphere at a predetermined oxygen partial pressure. The gas atmosphere may comprise a hydrogen/water mixture, a carbon monoxide/carbon dioxide mixture or an oxygen buffer in a closed system.

The invention also provides an alternative method for the manufacture of the secondary catalyst, the method comprising passing a gas atmosphere at a predetermined oxygen partial pressure over tungsten trioxide. The gas atmosphere may comprise a hydrogen/water mixture, a carbon monoxide/carbon dioxide mixture or an oxygen buffer in a closed system. It is preferred that the gas atmosphere comprise hydrogen/water in a ratio 40:1 arranged to flow over tungsten trioxide heated to 400° C. for 16 hours. The temperature may be varied between 200° C. and 900° C., preferably between 200° C. and 500° C. with consequential changes to the ratio of hydrogen and water.

It is also preferred that the tungsten trioxide first be formed on a suitable support. Preferably the support may comprise alpha-alumina or gamma-alumina. The tungsten trioxide may be formed on the support by impregnation of the support with a tungsten salt or with a slurry of tungsten trioxide powder. By way of example tungsten trioxide has been loaded onto supports in amounts up to 13 weight percent.

In one preferred method of forming tungsten trioxide on the support, the support is impregnated with sodium tungstate, dried, treated with concentrated nitric acid and then washed with dilute nitric acid. The sodium tungstate is converted to tungstic acid and then most of the sodium is eluted as the nitrate. After drying, the catalyst is heated to decompose the tungstic acid to form tungsten trioxide.

In another preferred method of forming tungsten trioxide, the support is impregnated with ammonium metatungstate, dried, and then heated to decompose the ammonium tungstate to form tungsten trioxide.

The present invention also provides a process for producing branched chain alkenes from straight chain alkenes, the process comprising passing a gaseous stream comprising a carrier gas and straight alkenes over the secondary catalyst. It is preferred that the secondary catalyst be heated to between 100° C. and 450° C. The selection of the temperature of the catalyst is dependent on the nature of the alkene and the reaction being performed. In general, branching of alkenes having carbon numbers approaching 8 is preferably carried out with the catalyst at a temperature between 150° C. and 200° C.; branching of shorter alkenes having carbon numbers towards 4 is preferably carried out with the catalyst heated at a temperature between 300° C. and 350° C.; and cracking of alkenes having carbon numbers greater than 8 is carried out with the catalyst heated to between 200° C. and 400° C.

The carrier gas may comprise argon, carbon dioxide, nitrogen or a carbon monoxide/carbon dioxide mixture. It is preferred that the carrier gas comprise a hydrogen/water mixture at a predetermined oxygen partial pressure. The process may be carried out at atmospheric pressure although higher pressures may be used.

The primary and secondary catalyst described above may be used in a continuous process for producing branched chain alkenes from a Fischer-Tropsch reactor for producing alkenes in a stream of alkenes, carbon monoxide and hydrogen. The product may be used to form the feed stock for the production of high octane fuel by alkylation. The product may also be used in the petro-chemical industry. In relation to the primary catalyst it should be recognised that use of the primary catalyst to catalyse reaction of carbon monoxide and hydrogen to form a significant proportion of the product as 1-alkenes makes the primary catalyst potentially suitable for use in synthesis processes in the petrochemical industry.

It should be readily apparent that the secondary catalyst described above may also be used for the conversion of straight chain alkenes produced by processes other than the Fischer-Tropsch process.

Having outlined the invention in broad terms, further details will be provided by way of specific examples which are provided herein for purposes of illustration only and are not intended to be limiting to the invention.

EXAMPLE 1

A sample of the primary catalyst was prepared and tested in the Fischer-Tropsch process. The sample of the primary catalyst comprised 2% iron (as Fe) and 3% praseodymium (as $Pr_6O_{11}$) impregnated as an alumina support and was tested under the following reaction conditions:

| | |
|---|---|
| Temperature: | 280° C. |
| Pressure: | 1200 KPa |
| Gas Hourly Space Velocity (GHSV) | 900 hr$^{-1}$ |
| Gas ratio $CO/H_2$ = | 2 |
| Alumina support: | α-alumina heat treated at 1250° C. for 10 minutes |

It was found that after an initial conditioning period of two hours the reaction products and activity of the sample of the primary catalyst were essentially constant over 600 hours. Gas chromatographic analysis showed that greater than 90% of the hydrocarbon reaction products were alkenes and less than 4% were methane gas. FIG. 1 is a graph illustrating the distribution of the carbon members of the hydrocarbons in the reaction product. It is evident from the figure that a significant proportion of the product comprises hydrocarbons having carbon numbers between 2 and 8.

Figure 2:
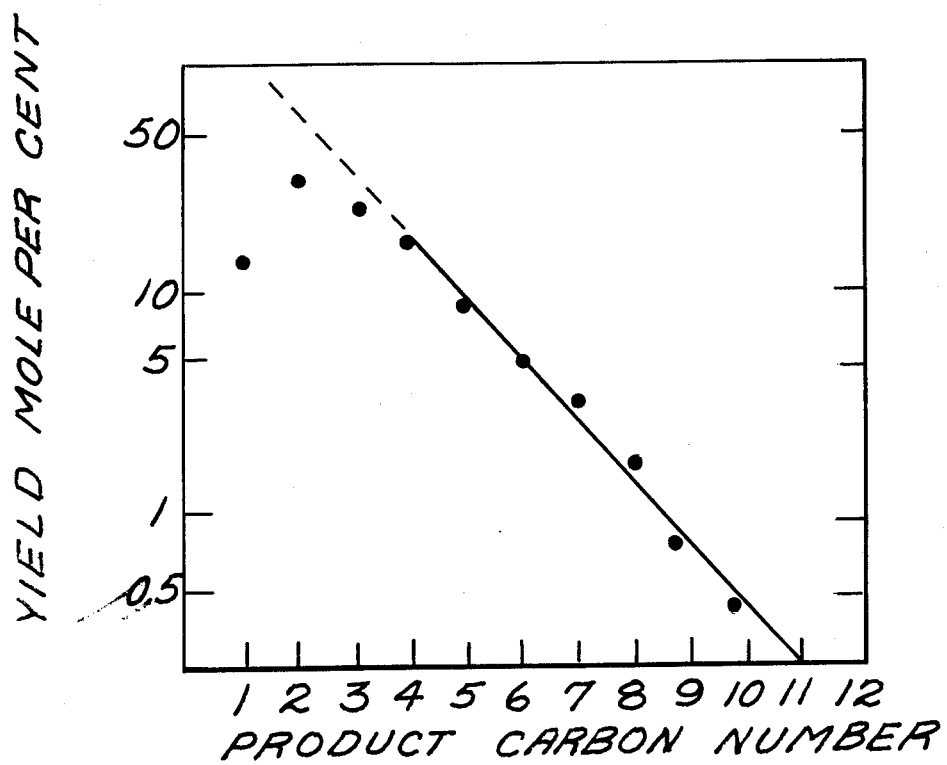
FIG. 2 is a graph of the yield, in mole percent, versus product carbon number.

It is known that carbon chain growth in the Fischer-Tropsch process commonly follows a Schultz-Flory mechanism which leads to a logarithmic relation between moles of reaction product and the carbon number of the reaction product. FIG. 2 is a plot of the product yield versus carbon number for the sample of primary catalyst tested and it is evident that there is a departure from the straight line expected under the Schultz-Flory mechanism for carbon numbers less than 4. This diminished production of light gaseous product is an important improvement over the results with conventional Fischer-Tropsch catalysts since it is achieved without excessive production of very high carbon number products.

EXAMPLE 2

Tables 1 to 4 sumarise experimental data in relation to primary catalysts prepared in accordance with the present invention. Before dealing with the experimental results in detail the following experimental procedures were followed in order to prepare the data:

1. Preparation of Catalyst Support

A catalyst support was prepared by heat treating granular γ-alumina in accordance with the following procedure:

Granular γ-alumina (Merck, anhydrous) was sieved and the 125–150μ fraction (~20% of total) retained and dried at 200° C. for 3 hr.

A large furnace set at 1250° C. was fitted with a rotatable alumina tube with the closed end positioned in the hot zone. A 20 g batch of the dried granular alumina was pre-heated at 750° C. in a silica tube in a separate furnace. The large furnace was tilted up to receive the 750° C. alumina sample, returned to the horizontal position with the thermocouple for the furnace controller inserted into the sample. The alumina tube was rotated during the heating stage within the furnace with the sample occasionally being stirred by the thermocouple. The temperature of the alumina sample rose from 750° C. to 1250° C. over a period of three to four minutes and then remained constant. Ten minutes after the alumina was placed in the 1250° C. furnace, the furnace was tilted down and the alumina discharged from the alumina tube into a platinum dish. Tests carried out on alumina samples heat treated in accordance with the above procedure indicate that:

1. The heat treated alumina has a surface area of 8 to 10 $m^2g^{-1}$ when formed when γ-alumina having an initial surface area of 70 $m^2g^{-1}$. This compares with known surface area of α-alumina which is generally less than 1 $m^2g^{-1}$.

2. The heat treated alumina gives an intense pink colour with phenolphthalein indicator which indicates that the surface of the heat treated alumina exhibits basic properties. The initial γ-$Al_2O_3$ and excessively heated alumina does not give this result.

3. X-ray diffraction analysis indicates that the crystallographic structure of the heat treated alumina predominantly comprises α-alumina.

2. Preparation of Modifier Component for Primary Catalyst (a) Praseodymium Nitrate Solution Praseodymium oxide, $Pr_6O_{11}$ (1.55 g) was weighed into a silica crucible, concentrated nitric acid (2.5 ml) added and heated on a hot plate until the oxide had dissolved and the acid evaporated (~2 hr). The crucible and contents were heated overnight in an oven at 100° C. The praseodymium nitrate was dissolved in water, transferred to a volumetric flask (25 ml) and made up to volume.

Note:
(1) 0.65 ml of the solution/g $Al_2O_3$ forms a 3% loading of praseodymium oxide, $Pr_6O_{11}$.
(2) pH of the solution is ~1.0.

(b) Technical Ceria Solution

Technical ceria, $CeO_2$ (AJAX) (4.0 g) was digested with concentrated nitric acid (30 mls) for about three hours. A very small amount of undissolved solid remaining was ignored. The solution was made up to 50 ml.

Note:
(1) 0.65 ml of the solution/g $Al_2O_3$ forms a 5% loading of rare earth oxides.
(2) AJAX Technical Ceria contains approximately equal amounts of lanthanum sesquioxide, $La_2O_3$ and cerium dioxide, $CeO_2$ with approximately 2% neodymium sesquioxide, $Nd_2O_3$ and 0.5% praseodymium oxide, $Pr_6O_{11}$.

3. Preparation of Active Component for Primary Catalyst (a) Ferric Nitrate Solution Ferric nitrate, $Fe(NO_3)_3 \cdot 9H_2O$ (11.0 g) was dissolved in water and made up to 50 ml.

Note:
(1) 0.65 ml of the solution/g $Al_2O_3$ forms a 2% loading of iron.
(2) pH of the solution is ~1.0.

4. Preparation of Primary Catalyst (a) (2% Fe/5% AJAX Technical Ceria/$Al_2O_3$)

Alumina oxide (10 g) pretreated in accordance with the procedure described under the heading "Preparation of Catalyst Support" was weighed into a silica crucible, the ceria solution (6.5 mls) added and mixed well with the aid of an ultrasonic bath. [When stirred with a spatula in an ultrasonic bath the mixture becomes very fluid. After the ultrasonic bath is switched off, continued stirring causes the alumina to reabsorb the free liquid]. Most of the alumina was transferred to a petrie dish, spread ~2 mm thick and, with the crucible, dried 20 hours in a vacuum dessicator. The alumina was returned to the crucible, dried 1 hour at 90° C. and fired for 1½ hours at 500° C. The ceria/alumina was impregnated with ferric nitrate solution (6.5 mls), mixed as above, dried under vacuum (20 hours) dried at 90° C. (1 hour) and fired at 450° C. (2 hours).

(b) 2% Fe/3% $PrO_x$/$Al_2O_3$ catalyst.

A similar procedure to (a) was followed.

5. Experimental Results

Tables 1 to 4 present the results of experimental work carried out on catalysts prepared in accordance with the procedures described in the foregoing, together with the results of experimental work carried out on conventional catalysts. The reaction conditions for experimental work are indicated in the tables and the details of the experimental reactor and precondition procedure are as follows:

Reactor

The samples of catalyst tested were placed in a stainless steel (type 316) tube 4 cm long with an internal diameter of 0.476 cm (3/16"). The reactor had a volume of 1.07 ml and typically held about 1.1 g of alumina supported catalyst. A stainless steel frit (type 316) with a pore size of 10μ was positioned at each end of the reactor. Carbon monoxide and hydrogen were flowed into the reactor from separate flow controllers upward through the catalyst bed to a stainless steel pressure control valve. All connecting tubing was made of copper.

Preconditioning

Prior to introduction into the reactor the catalyst samples were exposed to a stream of hydrogen at 400° C., atmospheric pressure and gas hourly space velocity of 1000 $hr^{-1}$ for 16 hours.

Table 1 illustrates the effect of heat treatment of the alumina support and the inclusion of praseodymium oxide on the properties of the catalyst.

The experimental results shown in Table 1 were prepared by positioning samples of the catalysts in the reactor and maintaining the following reaction conditions:

| | |
|---|---|
| Temperature: | 280° C. |
| Pressure: | 800 kPa |
| $CO/H_2$ = | 2 |
| Gas hourly space velocity (GHSV) = | 900 $hr^{-1}$ |

The table indicates that:

1. An improvement in catalyst properties can be realised by impregnating the active component on a γ-alumina support heat treated in accordance with the procedure outlined under the heading "Preparation of Catalyst Support". For example a catalyst comprising Fe impregnated on a heat treated γ-alumina support exhibits higher activity and better selectivity than a catalyst comprising 1.6 wt.% Fe impregnated on a conventional γ-alumina support. In this regard it should be noted that the activity increases from 0.3 to 10.4% CO converted to hydrocarbons in the first pass. Furthermore, it should be noted that the catalyst including the heat treated γ-alumina support results in a substantial reduction in undesirable methane formed in the product and a significant increase in preferred alkenes having carbon numbers between $C_2$ and $C_8$.

2. A further improvement in properties is obtained by impregnating the heat treated γ-alumina with both the active component and a modifier component such as praseodymium oxide. For example a catalyst comprising 2% Fe, 2% $Pr_6O_{11}$ impregnated on heat treated γ-alumina exhibits higher activity and better selectivity than catalysts which do not include praseodymium oxide.

TABLE 1

| Catalyst Composition | Fe wt. % | | 6.0 | 6.0 | 1.6 | 1.6 | 1.6 | 2.0 | 6.0 |
|---|---|---|---|---|---|---|---|---|---|
| | $Pr_6O_{11}$ wt. % | | — | 1.0 | — | — | — | 2.0 | — |
| | Support Type | | A | A | A | A | A | A | B |
| | Heat treatment °C./min | | — | — | — | 800/120 | 1250/10 | 1250/10 | — |
| CO converted to hydrocarbon (%) | | | ~14.0 at 300° C. | 2.4 at 300° C. | 0.3 | 0.3 | 10.4 | 14.7 | 12.3 |
| Weight Percent | | $C_1$ | 30.4 | 22.6 | 21.9 | 25.8 | 14.1 | 7.0 | 26.1 |
| | Alkenes | $C_2$ | 14.0 | 17.5 | 13.4 | 7.4 | 7.8 | 16.7 | 7.4 |
| | | $C_3$ | 17.6 | 22.9 | 18.4 | 15.9 | 17.1 | 25.6 | 17.7 |
| | | $C_4$ | 8.5 | 12.5 | 12.2 | 11.7 | 12.9 | 20.7 | 14.4 |
| | | $C_5$ | 2.6 | 6.9 | 6.0 | 3.3 | 11.8 | 6.0 | 9.3 |
| | | $C_6$ | 1.3 | 2.7 | 2.7 | 1.8 | 8.4 | 3.9 | 5.7 |
| | | $C_7+$ | 1.3 | 2.3 | 2.7 | 1.8 | 13.6 | 7.1 | 7.6 |
| | Alkanes | $C_2$ | 13.9 | 8.5 | 16.4 | 24.8 | 3.7 | 5.6 | 7.6 |
| | | $C_3$ | 5.9 | 2.3 | 2.8 | 3.4 | 2.5 | 1.5 | 3.4 |
| | | $C_4$ | 2.8 | 1.0 | 1.9 | 2.5 | 2.0 | 1.2 | 3.4 |
| | | $C_5$ | 0.9 | 0.5 | 0.9 | 0.7 | 2.1 | 1.4 | 2.8 |
| | | $C_6$ | 0.4 | 0.2 | 0.4 | 0.4 | 1.4 | 1.2 | 2.3 |

TABLE 1-continued

| | | $C_7+$ | 0.4 | 0.2 | 0.4 | 0.4 | 2.3 | 2.1 | 2.8 |

A = "Merck" γ-alumina
B = "Alfa" alumina

Table 2 illustrates the effect of a modifier component in catalysts comprising 2% Fe impregnated on a heat treated γ-alumina support on the product distribution resulting from tests carried out under conditions described in relation to Table 1.

The table illustrates that catalysts prepared with modifier components 1 to 4 of the invention exhibit better activity and selectivity properties than a catalyst prepared with a conventional modifier component 5 comprising 1.8 wt% $K_2O$. In particular, it should be noted that the catalysts which include modifier components of the invention catalyst the formation of product distributions which have significantly lower amounts of methane and alkanes than in the case with a catalyst which includes a conventional modifier component.

Table 3 illustrates the effect of reaction conditions on product distribution for catalysts comprising 1.6 wt% Fe and 1.0 wt% $Pr_6O_{11}$ impregnated on a heat treated γ-alumina support (1–4) and catalysts comprising 1.6 wt% Fe and 2.0 wt% $Pr_6O_{11}$ impregnated on a heat treated γ-alumina support (5–7). In particular, the table indicates that as the reaction temperature increases there is a significant increase in activity with only a marginal deterioration in selectivity. (cf sample 5 and 7).

TABLE 3

| | | | | | | | | |
|---|---|---|---|---|---|---|---|---|
| Temperature (°C.) | | 260 | 260 | 260 | 280 | 280 | 300 | 320 |
| GHSV ($hr^{-1}$) | | 1800 | 1800 | 900 | 900 | 900 | 900 | 900 |
| Pressure ($KP_a$) | | 1240 | 800 | 800 | 800 | 800 | 800 | 800 |
| $CO/H_2$ | | 2.0 | 2.0 | 2.0 | 2.0 | 2.0 | 2.0 | 2.0 |
| CO converted to hydrocarbon (%) | | 2.9 | 2.5 | 5.2 | 16.8 | 12.5 | 22.6 | 37.2 |
| Weight Percent | $C_1$ | 7.3 | 8.6 | 7.3 | 8.0 | 5.0 | 6.0 | 8.6 |
| Alkenes | $C_2$ | 7.8 | 9.2 | 7.7 | 7.0 | 15.0 | 14.8 | 16.0 |
| | $C_3$ | 13.1 | 15.3 | 14.5 | 15.4 | 23.8 | 23.8 | 24.4 |
| | $C_4$ | 12.0 | 13.2 | 13.2 | 13.9 | 17.5 | 16.1 | 15.2 |
| | $C_5$ | 11.1 | 10.8 | 12.4 | 12.1 | 12.0 | 11.3 | 10.0 |
| | $C_6$ | 7.9 | 7.5 | 8.0 | 5.7 | 8.0 | 7.1 | 6.0 |
| | $C_7+$ | 26.7 | 22.5 | 22.1 | 15.3 | 14.8 | 15.1 | 11.7 |
| Alkanes | $C_2$ | 3.4 | 4.0 | 3.1 | 2.9 | 0.9 | 0.6 | 1.3 |
| | $C_3$ | 2.1 | 2.3 | 2.2 | 1.8 | 1.0 | 1.4 | 2.0 |
| | $C_4$ | 2.0 | 2.2 | 2.0 | 1.9 | 0.7 | 1.0 | 1.2 |
| | $C_5$ | 1.6 | 1.1 | 2.2 | 2.3 | 0.6 | 0.8 | 0.9 |
| | $C_6$ | 1.1 | 0.8 | 1.4 | 1.1 | 0.5 | 0.7 | 1.0 |
| | $C_7+$ | 3.8 | 2.5 | 4.0 | 2.8 | 0.9 | 1.4 | 2.0 |

TABLE 2

| Catalyst Modifier | | (1) 3% $Pr_6O_{11}$ | (2) 5% Ceria (Tech. Grade) | (3) 3% Tech. Ceria (depleted) | (4) 3% $La_2O_3$ | (5) 1.8% $K_2O$ |
|---|---|---|---|---|---|---|
| CO converted to hydrocarbon (%) | | 5.4 | 2.6 | 3.9 | 2.5 | 0.6 |
| Weight Percent | $C_1$ | 4.8 | 7.5 | 5.1 | 6.0 | 27.6 |
| Alkenes | $C_2$ | 13.8 | 16.2 | 9.4 | 12.2 | 11.8 |
| | $C_3$ | 19.5 | 22.2 | 16.7 | 17.8 | 17.4 |
| | $C_4$ | 17.8 | 19.2 | 13.8 | 16.3 | 9.0 |
| | $C_5$ | 14.1 | 13.3 | 13.0 | 16.0 | 6.6 |
| | $C_6$ | 10.2 | 8.5 | 8.6 | 10.0 | 5.1 |
| | $C_7+$ | 17.6 | 12.9 | 14.4 | 11.5 | 6.4 |
| Alkanes | $C_2$ | 0.6 | 0.2 | 4.7 | 4.1 | 5.9 |
| | $C_3$ | 0.8 | 0.3 | 3.0 | 2.3 | 1.2 |
| | $C_4$ | 0.5 | 0.3 | 3.2 | 1.2 | 3.1 |
| | $C_5$ | 0.3 | 0.1 | 3.0 | 1.1 | 2.8 |
| | $C_6$ | 0.1 | 0.1 | 2.0 | 0.7 | 2.3 |
| | $C_7+$ | — | — | 3.3 | 0.8 | 1.0 |

Table 4 illustrates the effect of the $CO_2/H_2$ ratio on activity and product distribution. The catalyst tested comprised 1.6% wt%Fe and 1.0 wt% $Pr_6O_{11}$ impregnated on heat treated γ-alumina. The significant point evident from the table is that an excess of hydogen still results in the formation of alkenes as the major product.

TABLE 4

| | | | | | | | |
|---|---|---|---|---|---|---|---|
| Temperature (°C.) | | 260 | 280 | 240 | 260 | 260 | 260 |
| GHSV ($hr^{-1}$) | | 900 | 900 | 900 | 900 | 900 | 900 |
| Pressure ($KP_a$) | | 800 | 800 | 800 | 800 | 800 | 800 |
| $CO/H_2$ | | 2 | 2 | 0.5 | 0.5 | 2 | 0.5 |
| CO converted to hydrocarbon (%) | | 5.1 | 15.6 | 4.8 | 12.8 | 3.6 | 17.4 |
| Weight Percent | $C_1$ | 6.9 | 7.4 | 10.2 | 13.0 | 6.6 | 15.6 |
| Alkenes | $C_2$ | 9.4 | 6.9 | 8.0 | 6.1 | 9.8 | 4.9 |
| | $C_3$ | 15.0 | 15.3 | 14.3 | 16.7 | 14.9 | 16.6 |
| | $C_4$ | 13.1 | 13.7 | 11.4 | 12.4 | 13.5 | 12.3 |
| | $C_5$ | 12.7 | 13.5 | 11.8 | 11.7 | 14.2 | 10.1 |
| | $C_6$ | 8.8 | 9.9 | 7.4 | 7.2 | 11.6 | 6.5 |

TABLE 4-continued

|         |        |      |      |      |     |      |      |
|---------|--------|------|------|------|-----|------|------|
|         | $C_7+$ | 24.0 | 19.6 | 17.2 | 9.2 | 21.9 | 11.1 |
| Alkanes | $C_2$  | 2.8  | 2.3  | 4.0  | 8.0 | 3.0  | 7.1  |
|         | $C_3$  | 1.9  | 1.8  | 3.0  | 3.5 | 1.7  | 3.5  |
|         | $C_4$  | 1.5  | 2.1  | 2.6  | 3.4 | 1.1  | 3.3  |
|         | $C_5$  | 1.1  | 2.2  | 3.1  | 3.5 | 0.5  | 3.1  |
|         | $C_6$  | 0.8  | 1.7  | 2.1  | 2.4 | 0.3  | 2.2  |
|         | $C_7+$ | 2.3  | 3.3  | 4.9  | 3.0 | 0.9  | 3.7  |
| Mole ratio $CO_2H_2O$ |        |      |      |      |     | 2.83 | 1.27 |

EXAMPLE 3

Secondary Catalyst

Samples of the secondary catalyst comprising an intermediate oxide of tungsten were prepared and tested to investigate the effect of the catalyst on specific 1-alkenes. The intermediate oxide comprised $WO_x$, where $x = 2.8 \pm 0.15$.

Both supported and unsupported samples of the secondary catalyst were prepared.

The supported samples were prepared by impregnating alumina supports with sodium tungstate in accordance with the following procedures:

(a) Sodium Tungstate Solution

Sodium tungstate, $Na_2WO_4 \cdot 2H_2O$ (6.56 g) was dissolved in water and made up to 50 ml. Note: (1) 0.65 ml of the solution/g of $Al_2O_3$ formed a 6% loading of tungsten trioxide, $WO_3$.

(b) Preparation of 6% Tunsten Trioxide on Alumina

Alumina (10 g, thermally treated as previously described) was weighed into a 250 ml beaker, sodium tungstate solution (6.5 ml) added and the mixture stirred with the aid of ultrasonic agitation. The sample was dried in a vacuum dessicator (~4 hour) and in air at 90° C. (1 hour). Concentrated nitric acid (10 ml) was added and the beaker warmed on a hot plate for 5 minutes and the solid was then washed with ~1M nitric acid by decantation. To remove sodium nitrate, 1M nitric acid (250 mls) was added, the catalyst digested for 1 hour on a hot plate and the nitric acid decanted. This washing was repeated three times and the catalyst dried at 150°–160° C.

The $WO_3$ was reduced to $WO_{2.9}$ by reduction with wet hydrogen. The catalyst was placed on a glass frit in a pyrex tube and heated to about 400° C. Hydrogen was bubbled through water at rom temperature and then up through the heated catalyst at a flow rate of 200 ml/min. The catalyst was reduced for 4 hours at 400° C.; it was then blue and was cooled and stored.

(c) Preconditioning

The catalyst in the reactor was heated for 1 hour in a stream of wet hydrogen (obtained by bubbling hydrogen through water at room temperature) under the following conditions:

| Temperature | 400° C. |
| Pressure | 100 kPa |
| Gas hourly space velocity | 900 hr$^{-1}$ |

The specific 1-alkenes tested comprised but-1-ene; pent-1-ene and hex-1-ene. The alkenes were separately introduced into a gaseous hydrogen/water mixture and passed over the samples of secondary catalyst heated to 300° C. at a flow rate of 10 cm$^3$min$^{-1}$ and at a pressure of 100 kPa.

The alkenes were introduced into the hydrogen stream by inserting a bubbler containing the alkene, upstream from the bubbler containing water. The bubbler containing the alkene was cooled in a solid/liquid bath at an appropriate temperature to set the alkene vapor pressure at 10 mm Hg. Chlorobenzene was found to be an appropriate bath for 1-pentene and chloroform was found to be suitable for 1-hexene. (An alternative method which is less quantitative involves collection of vapour from a solution of alkene in a low vapor pressure paraffin oil). The hydrogen stream thus picked up the alkene, was then saturated with water and flowed over the catalyst under the conditions described above.

A summary of an analysis of the reaction products for each of the 1-alkenes is shown in Table 5.

TABLE 5

| REACTANT | PRODUCTS | % | |
|----------|----------|---|---|
| But-1-ene | But-1-ene | 9 | |
|  | But-2-ene | 43 | } 57 |
|  | Butane | 5 | |
|  | 2 Methyl propene | 38 | } 43 |
|  | 2 Methyl propane | 5 | |
| Pent-1-ene | Pent-1-ene | 1 | |
|  | Pent-1-ene | 32 | } 34 |
|  | Pentane | 1 | |
|  | 2 Methyl but-2-ene | 58 | |
|  | 2 Methyl but-1-ene | 1 | } 66 |
|  | 2 Methyl butane | 2 | |
|  | 2 Methyl propane | 5 | |
| Hex-1-ene | Hex-1-ene | 6 | |
|  | Hex-2-ene | 15 | } 26 |
|  | Hexane | 5 | |
|  | 3 Methyl pent-2-ene | 59 | |
|  | 2 Methyl pent-1-ene | 2 | } 74 |
|  | 2,3 Dimethyl but-2-ene | 6 | |
|  | 3 Methyl pentane | 7 | |

The table indicates that conversions from the 1-alkene to branched alkenes increased with increasing carbon number of the 1-alkene. For example, 38% of the product formed from but-1-ene comprised 2-methyl propene whereas 58% of the product formed from pent-1-ene comprised 2 methyl but-2-ene.

EXAMPLE 4

Samples of the secondary catalyst prepared in Example 3 were tested to investigate the effect of the catalyst on a feed stream of 1-octene. Reaction conditions were as follows:

| Loading of the intermediate oxide of tungsten: | 6% by weight on alumina support |
| Temperature: | 300° C. |
| Pressure: | 100 kPa |
| Flow rate: | 100 cc/min $H_2/H_2O/1$-octene |

A summary of an analysis of the reaction products is shown in Table 6.

TABLE 6

Products from the cracking and
isomerization of 1-octene over a 6%
tungsten catalyst. 300° C., 1
atmosphere, 100 cc min $H_2/H_2O$/1-octene.

| Reactant | Products* | Wt. % |
|---|---|---|
| OCT-1-ENE | C1 | — |
|  | C2 | — |
|  | C3 | 4.1 |
|  | C4 | 39.8 |
|  | C5 | 8.0 |
|  | C6 | 3.6 |
|  | C7 | 2.9 |
|  | C8 | 41.6 |
|  | C9 | — |

*95% products branched.

EXAMPLE 5

Samples of the secondary catalyst prepared in Example 3 were tested to investigate the effect of the secondary catalyst on higher carbon number hydrocarbons, specifically 1-dodecene ($C_{12}$). The 1-dodecene was included in a gaseous hydrogen/water mixture and passed over samples of the supported secondary catalyst, under the following experimental conditions:

| | |
|---|---|
| Catalyst weight: | approx 1 g |
| Loading of the intermediate oxide of tungsten: | 13% by weight on alumina support |
| Ratio $H_2/H_2O$: | 40:1 |
| Pressure: | 100 kPa |
| Gas space velocity: | 600 $hr^{-1}$ |
| Alkene loading 0.03-0.01 g/g of catalyst/hour | |

Figure 3:
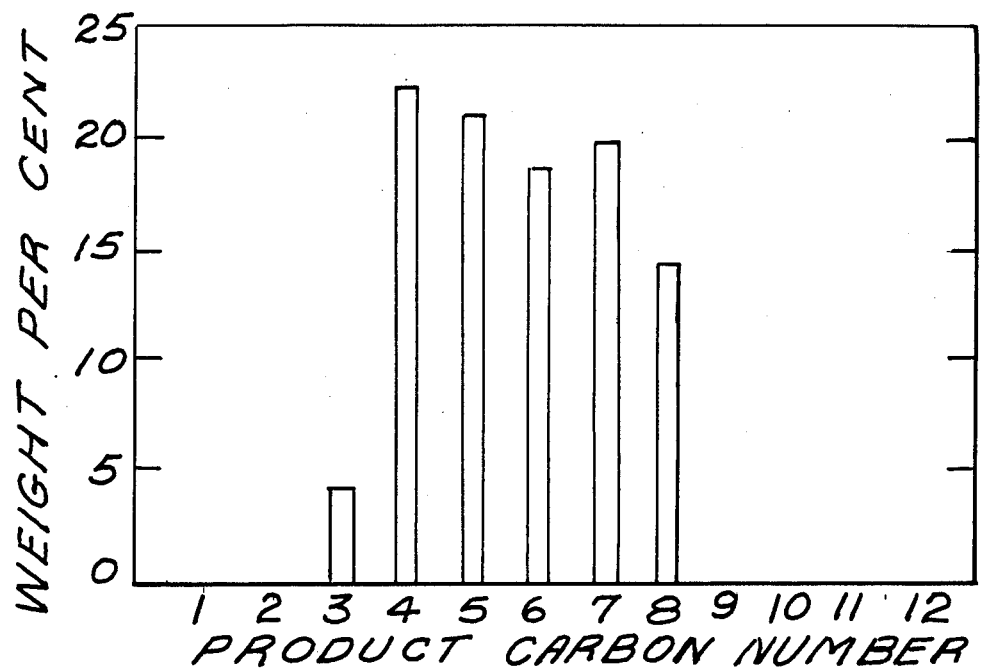
FIG. 3 is a plot of the weight percent of products versus product carbon number.

The result of an analysis of the reaction products is shown in FIG. 3 which is a plot of the weight percent of products versus product carbon number. FIG. 3 illustrates that the secondary catalyst cracked the 1-dodecene and caused reactions to form branched alkenes having carbon numbers predominantly in the range 4 to 8.

It was also found in further experiments that similar results were obtained for higher loadings of alkene although at lower temperatures the conversion to branched alkenes falls as the alkene content in the hydrogen/water carrier increases. The results indicate that high conversions can be obtained with the alkene loading in excess of 0.5 g alkene/gram of catalyst/hour.

It was found that the life of the secondary catalyst is limited to a few hours when cracking is occurring. This is believed to be caused by the deposition of coke on the surface of the secondary catalyst. Regeneration of the surface may be performed quickly by raising the temperature of the catalyst to 450° C. or above while flowing a stream of air or other oxidizing gas over the secondary catalyst. Under experimental conditions it was found that regeneration could be completed after four minutes of flowing a stream of air at 450° C.

EXAMPLE 6

Figure 4:
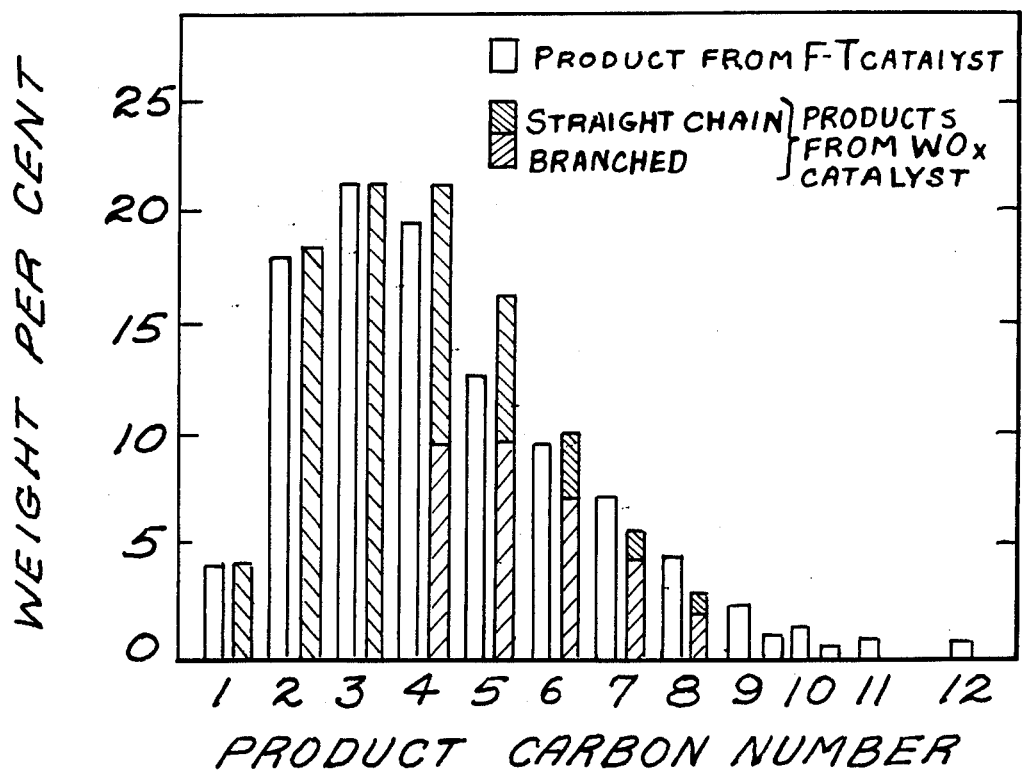
FIG. 4 is a plot of weight percent of product versus product carbon number.

Samples of the secondary catalyst described in Example 3 were tested to investigate the effect of the catalyst on a Fischer-Tropsch product stream. In this regard, synthesis gas was passed over the primary Fischer-Tropsch catalyst which was operated at 800 kPa. The products from this catalyst passed through a pressure control valve (downstream from the catalyst) through a coil of copper tubing (1 meter) at room temperature and over the tungsten oxide catalyst operated at atmospheric pressure. The product stream was subsequently analysed and the results are shown in FIG. 4, which is a plot of weight percent of product versus product carbon number. For comparative purposes the figure also includes the results of the analysis for the product stream directly leaving the Fischer-Tropsch process and prior to being directed over the secondary catalyst.

It is evident from FIG. 4 that the secondary catalyst caused significant production of branched chain alkenes having carbon numbers between 4 to 8. In addition, there was an increase in the product between carbon numbers 4 and 6 due to cracking of the higher alkenes.

Note: Any products greater than C9 were trapped in the coil, limiting the extent of poisoning of the tungsten oxide catalyst by cracking. Operation life under these conditions was 3 hours (after which the catalyst should be regenerated). The tungsten oxide catalyst was regenerated by heating it to 450° C. (or above) for 5 minutes while flowing air through it with a space velocity of 10,000 $hr^{-1}$. Heating to this temperature and cooling to operating temperature was performed as quickly as possible. As soon as the catalyst had cooled the Fischer-Tropsch stream was re-connected and isomerisation recommenced immediately.

Those skilled in the art will appreciate that the invention described herein is susceptible to variations and modifications other than those specifically described. It is to be understood that the invention includes all such variations and modifications within its spirit and scope.

We claim:

1. A process for converting a feed stream comprising carbon monoxide and hydrogen into hydrocarbons, said process comprising passing said feed stream over a catalyst such that a significant proportion of the hydrocarbons formed are 1-alkenes having carbon numbers between 3 and 8 and greater than 90% of the hydrocarbons formed have carbon numbers between 2 and 8 and less than 6% of the hydrocarbons formed comprise methane, said catalyst comprising:

as a support, a heat-treated alumina material having a crystallographic structure predominantly indicative of α-alumina, and a surface area intermediate γ-alumina and α-alumina, said material exhibiting basic properties at the surface thereof, an active component comprising iron deposited on the support for catalyzing the reaction in said feed stream to produce said hydrocarbons, and a modifier component comprising a rare earth metal deposited on the support to modify the catalytic behavior of the active component to control the length of hydrocarbon chains formed by the reaction.

2. The process of claim 1 wherein the rare earth metal is praseodymium, present alone, or present with other rare earth metals in mixed rare earth oxides.

3. The process of claim 1 wherein the support is in granular or pellet form.

* * * * *